United States Patent [19]

Akers

[11] Patent Number: 4,485,806

[45] Date of Patent: Dec. 4, 1984

[54] METHOD AND APPARATUS FOR EVACUATING CONTAMINATED CASUALTIES

[75] Inventor: Charles K. Akers, Williamsville, N.Y.

[73] Assignee: Calspan Corporation, Buffalo, N.Y.

[21] Appl. No.: 544,347

[22] Filed: Oct. 24, 1983

[51] Int. Cl.³ .............................................. A61B 19/00

[52] U.S. Cl. .................................................... 128/1 R

[58] Field of Search .................. 128/1 R, 205.26, 1 B; 2/69, 69.5, 2 R

[56] References Cited

U.S. PATENT DOCUMENTS

| | | | |
|---|---|---|---|
| 2,700,384 | 1/1955 | Ivory | 128/1 R X |
| 3,492,987 | 2/1970 | Parker | 128/1 R |
| 3,678,921 | 7/1972 | Brendgoma et al. | 128/1 R |
| 3,850,172 | 11/1974 | Cazalis | 128/1 R |
| 4,275,719 | 6/1981 | Mayer | 128/1 R X |
| 4,335,712 | 6/1982 | Trexler | 128/1 R |
| 4,366,809 | 1/1983 | Trexler | 128/1 R |
| 4,367,728 | 1/1983 | Mutke | 128/1 R |

*Primary Examiner*—Edward M. Coven
*Attorney, Agent, or Firm*—Biebel, French & Nauman

[57] ABSTRACT

A contaminated casualty is enclosed within an evacuation container comprising inner and outer enclosures for evacuation to an uncontaminated treatment enclosure having an opening operably opened and closed by a first fastener. A second fastener operably opens and closes casualty entry openings in the inner and outer enclosures. The second fastener closes the space between the inner and outer enclosures to maintain uncontaminated space therebetween when the casualty entry openings are opened. A third fastener operably opens and closes a casualty extraction opening in the outer enclosure. The third fastener is compatible with at least a portion of the first fastener to form a passageway for moving a casualty encapsulated within the inner enclosure out from the outer enclosure and into the uncontaminated treatment enclosure.

7 Claims, 7 Drawing Figures

100
102
104
106
108
110
112
114
116
118
120
122
124
136
137

METHOD AND APPARATUS FOR EVACUATING CONTAMINATED CASUALTIES

BACKGROUND OF THE INVENTION

This invention relates generally to the evacuation of contaminated casualties from a chemically contaminated environment and, more particularly, to the protection of attending personnel during evacuation, treatment and decontamination of such casualties.

Within the scope of personnel protection against a chemically contaminated environment, such as would result from chemical warfare or hazardous chemical spill, the protection of individuals is a high priority. Effective protection of individuals is provided by a protective garment which includes a sealed face mask and respiration system to filter and purify air drawn into the garment. Unfortunately, protective garments can be damaged and oftentimes many persons within an area which becomes chemically contaminated do not have the benefit of protective garments. These vulnerable persons become casualties of the chemical contamination and are referred to herein as contaminated casualties.

When a contaminated casualty is discovered, it is imperative to the survival of the casualty that decontamination and medical treatment be obtained as early as possible. For treatment, a casualty must initially be transported to an uncontaminated treatment enclosure, be decontaminated and then passed into the treatment enclosure. Of course, attending personnel must be protected from contamination during contact with contaminated casualties.

A presently accepted method for decontaminating a casualty and passing the casualty into a treatment enclosure is by means of an airlock system. The airlock concept requires a minimum of two doorways and a separate intermediate compartment sufficiently large to accommodate decontamination by attending personnel. The airlock concept also greatly increases the demand for filtered air for ventilating and purging the airlock compartment. This additional requirement results in a major increase in the size and cost of the air purification equipment necessary for the operation of the treatment enclosure.

An additional problem with airlock systems is that they provide for safe entry of only one or a small number of casualties at a time. Further, a relatively large time interval, on the order of 10 to 15 minutes, is required to safely and completely execute the entry procedures for a treatment enclosure equipped with a conventional positive pressure airlock system.

Rapid entrance and egress of personnel encapsulated in protective garments into and out of treatment enclosures or other protective shelters, as well as the treatment of casualties encapsulated within such protective garments by moving them into larger protective shelters, was addressed by U.S. patent application Ser. No. 390,100, filed June 21, 1982, and assigned to the same assignee as the present application. Also, the treatment of casualties encapsulated in protective garments while in a chemically contaminated environment was addressed by U.S. patent application Ser. No. 501,733, filed June 6, 1983, and assigned to the same assignee as the present application. However, these applications address neither the problem of evacuating contaminated casualties which are not encapsulated in protective garments from a chemically contaminated area nor the protection of attending personnel during evacuation, treatment and decontamination of such casualties.

Accordingly, the need exists for a method and apparatus for rapid evacuation, treatment and decontamination of contaminated casualties from a chemically contaminated environment which assures protection of attending personnel.

SUMMARY OF THE INVENTION

In accordance with the present invention, a contaminated casualty is evacuated to an uncontaminated treatment enclosure by means of a casualty evacuation container. The treatment enclosure has at least one opening with first fastener means connected to and operable for opening and closing the opening. The casualty evacuation container has inner and outer enclosures with the inner enclosure fitted inside the outer enclosure. Both inner and outer enclosures have a casualty entry opening therethrough with second fastener means attached to and operable for opening and closing the casualty entry openings. The second fastener means provides for closing the space between the inner and outer enclosures when the casualty entry openings are opened. Accordingly, the space between the inner and outer enclosures remains uncontaminated while the interior of the inner enclosure is opened to receive a contaminated casualty.

A casualty extraction opening is provided in the outer enclosure and third fastener means are attached to and operable for opening and closing the casualty extraction opening. The third fastener means are compatible with at least a portion of the first fastener for opening and closing the uncontaminated treatment enclosure into which the contaminated casualty is to be evacuated.

In accordance with the present invention, a contaminated casualty is safely evacuated to a treatment enclosure by: opening the casualty entry openings in the inner and outer enclosures forming the casualty evacuation container with the space therebetween being closed to remain uncontaminated; placing a casualty into the interior of the inner enclosure; operating the second fastener means to thereby close the casualty entry openings to enclose the contaminated casualty within the inner and outer enclosures; transporting the casualty in the casualty evacuation container; securing the third fastener means of the casualty extraction opening to the first fastener means of the treatment enclosure to thereby form a passageway between the interior of the outer enclosure and the interior of the treatment enclosure; and moving the casualty encapsulated within the inner enclosure through the casualty extraction opening into the uncontaminated treatment enclosure for decontamination and/or treatment of the casualty.

For proper operation, the fastener means must be formed into flexible panels of the enclosures and preferably the inner and outer enclosures comprise bags with the flexible panels comprising side walls of the bags.

Preferably, at least the second fastener means uses pairs of compatible zipper-type fasteners with a slider combining the pairs of fasteners in such a manner that while the fastener pairs are being opened at one end of the slider, opposite adjacent members of those pairs are being joined together at the opposite end. To achieve this, the slide member embraces both fasteners and disconnects the zipper tape pairs in the conventional manner, but then the tape members are twisted or rotated 90° before reattachment. The 90° rotation causes each tape member from one pair to be aligned with a mating tape member from the other pair to which it is then joined.

This type fastener advantageously performs the operation of closing the space between the inner and outer enclosures while the interior of the inner enclosure is exposed through the casualty entry openings of the inner and outer enclosures and then separating the inner and outer enclosures as the casualty entry openings are closed. A chemically contaminated casualty enclosed or encapsulated within the inner enclosure can then be removed rapidly from the outer enclosure by joining the outer enclosure to an uncontaminated treatment enclosure by means of the third fastener means surrounding the casualty extraction opening. Thus, in accordance with the present invention, the contamination of the contaminated casualty is safely retained within the inner enclosure.

Once the chemically contaminated casualty encapsulated within the inner enclosure has been moved into the uncontaminated treatment enclosure, treatment and/or decontamination can be safely performed by means of access apparatus. The access apparatus comprises a treatment container which may be fastened to at least a portion of the second fastener means of the inner enclosure to thereby open the inner enclosure to the interior of the container. The container includes handling means for permitting sealed insertion of the hands of attending personnel into the interior of the container and the inner enclosure. Also, an observation window is included in the container such that attending personnel can observe the casualty and the decontamination and/or treatment operations.

In lieu of a separate container for decontaminating and/or treating a contaminated casualty encapsulated within the inner enclosure, the inner enclosure may include treatment means therewithin and handling means for permitting sealed manipulation within the inner enclosure by attending personnel.

It is therefore an object of the present invention to provide a method and apparatus for evacuating contaminated casualties to an uncontaminated treatment enclosure by means of a casualty evacuation container comprising inner and outer enclosures inserted one within the other and having fastener means surrounding casualty entry openings therethrough for opening the interior of the inner enclosure while sealing the space between the inner and outer enclosures to prevent contamination of the space therebetween, closing the inner and outer enclosures to encapsulate the contaminated casualty within the inner and outer enclosures, and separating the inner and outer enclosures such that the contaminated casualty encapsulated within the inner enclosure may be removed through a casualty extraction opening through the outer enclosure which includes fastener means adapted to engage fastener means of the uncontaminated treatment enclosure to permit passage of the contaminated casualty encapsulated within the inner enclosure into the uncontaminated treatment enclosure wherein the contaminated casualty may be decontaminated through the use of treatment container means which engages the fastener means of the inner enclosure thus protecting personnel attending the evacuation, treatment and decontamination of the contaminated casualty.

Other objects and advantages of the invention will be apparent from the following description, the accompanying drawings and the appended claims.

DETAILED DESCRIPTION OF THE INVENTION

Figures 1, 2, 3, 4:
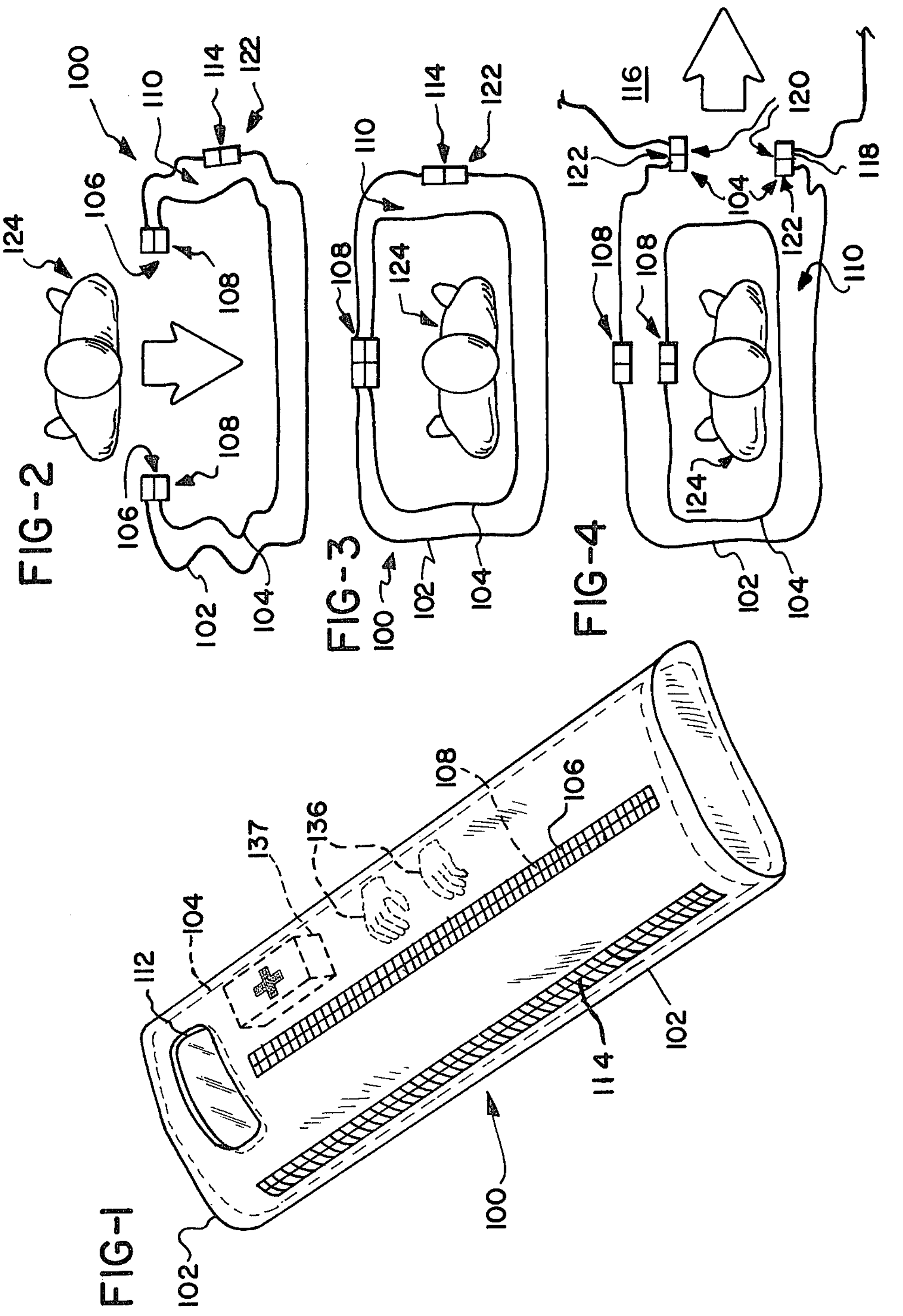
FIG. 1 is a perspective view of the apparatus in accordance with the present invention.
FIGS. 2 through 4 are a cross-sectional view of the apparatus of FIG. 1 showing the method of the present invention for the evacuation of a contaminated casualty.

A casualty evacuation container 100 in accordance with the present invention is shown in FIG. 1. The casualty evacuation container comprises an outer enclosure 102 and an inner enclosure 104. Both the inner enclosure 104 and the outer enclosure 102 have casualty entry openings 106 therein (also see FIG. 2) and the inner enclosure is fitted within the outer enclosure with the casualty entry openings aligned with one another. Fastener means 108 are attached to the casualty entry openings in the inner and outer enclosures 104, 102 and serve to open and close the casualty entry openings 106 to permit access to the interior of the inner enclosure 104.

As best seen in FIG. 2, when the inner and outer enclosures 104, 102 are open to permit access to the interior of the inner enclosure 104, the space between the inner and outer enclosures 104, 102 is closed by the fastener means 108. This prevents the interior space 110 between the inner and outer enclosures from being contaminated while permitting access to the interior of the inner enclosure 104. Preferably, observation windows 112 are included in the inner and outer enclosures 104, 102 to permit a contaminated casualty to view the outside world and, hence, realize that he or she is being assisted.

A casualty extraction opening 114 is provided in the outer enclosure 102 to permit a contaminated casualty encapsulated within the inner enclosure 104 to be safely removed to the interior of an uncontaminated treatment enclosure 116. The treatment enclosure 116 includes fastener means 118 connected to a casualty entry opening 120 for operably opening and closing the casualty entry opening.

The casualty extraction opening 114 is surrounded by fastener means 122 for opening and closing the casualty extraction opening 114 in the outer enclosure 102. The fastener means 118 are compatible with the fastener means 122 to form a passageway between the interior space 110 of the outer enclosure 102 and the interior of the treatment enclosure 116 by interconnecting the casualty entry opening 120 in the treatment enclosure with the casualty extraction opening 114 in the outer enclosure 102.

The method for evacuating contaminated casualties utilizing the disclosed apparatus will now be described with reference to FIGS. 2 through 4. A contaminated casualty 124 to be evacuated to an uncontaminated treatment enclosure 116 is initially located in a contaminated environment. A casualty evacuation container 100 comprising inner and outer enclosures 104, 102 is brought to the casualty 124 and the casualty entry openings 106 are opened by the fastener means 108 which closes the space 110 between the inner and outer enclosures as the casualty entry openings 106 are opened. The casualty evacuation container 100 is shown opened in FIG. 2.

The contaminated casualty 124 is placed within the inner and outer enclosures 104, 102 through the casualty entry openings 106. The fastener means 108 is then operated to close the casualty entry openings 106 in the inner and outer enclosures 104, 102 such that the contaminated casualty 124 is encapsulated within the inner enclosure 104 which is in turn encapsulated within the outer enclosure 102. The fastener means 108 is such that the inner and outer enclosures 104 and 102 may be completely separated from one another as shown in FIG. 4.

The contaminated casualty 124 thus encapsulated is transported to the uncontaminated treatment enclosure 116. The fastener means 118 around the casualty entry opening 120 of the treatment enclosure 116 is engaged with the fastener means 122 around the casualty extraction opening 114 of the outer enclosure 102. The engaged fastener means 118 and 122 are operated to form a closed passage between the interior 110 of the outer enclosure 102 and the interior of the treatment space 116' as shown in FIG. 4.

The contaminated casualty 124 encapsulated within the inner enclosure 104 is then moved into the uncontaminated treatment enclosure 116. Since the space 110 between the outer enclosure 102 and the inner enclosure 104 has been maintained in an uncontaminated condition, the outer surface of the inner enclosure 104 is uncontaminated and can be safely handled by attending personnel within the uncontaminated treatment enclosure 116.

Figure 5:
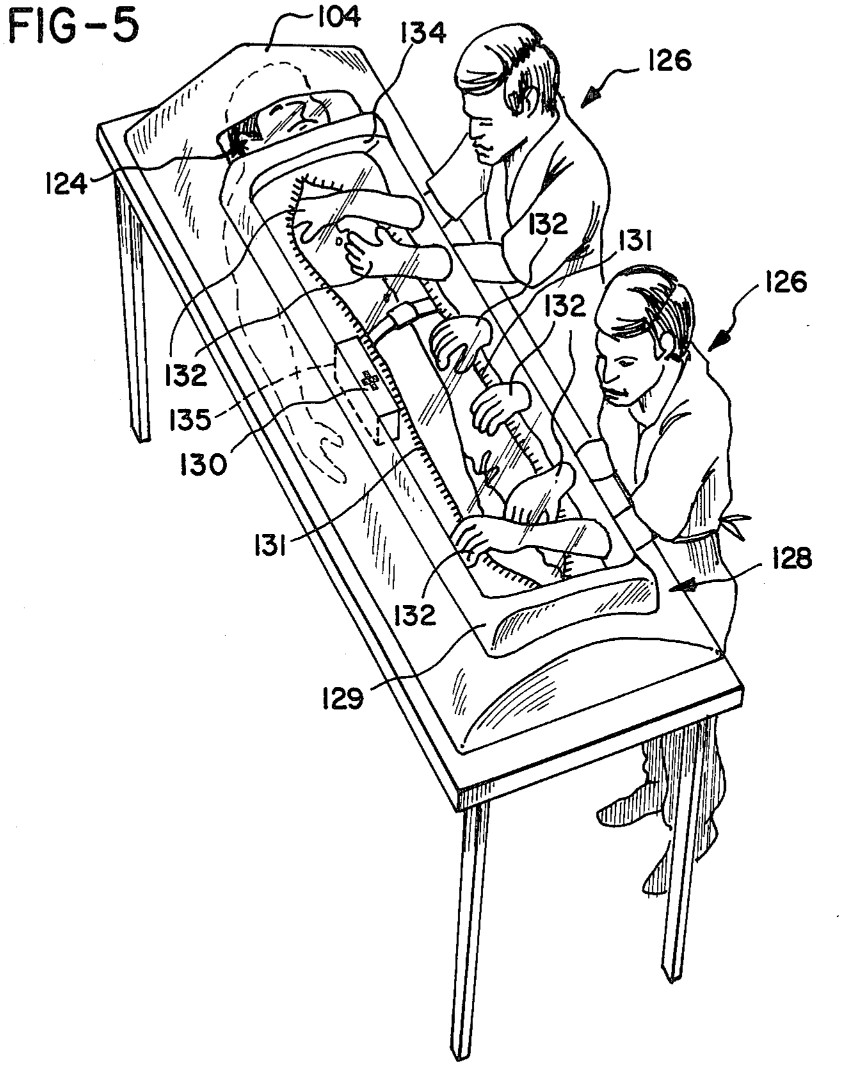
FIG. 5 is a perspective view of the initial treatment/decontamination of a contaminated casualty within a treatment enclosure.

As shown in FIG. 5, personnel 126 may attend to the casualty 124 by means of access apparatus 128. The access apparatus 128 comprises a treatment container 129 having a flexible base panel 130 with an opening therethrough surrounded by fastener means 131 which may be connected to at least a portion of the fastener means 108 surrounding the casualty entry opening 106 in the inner enclosure 104.

As the fastener means 131 is connected to the fastener means 108, the treatment container 129 is connected to the inner enclosure 104 and the interior of the treatment container 129 is opened to the interior of the inner enclosure 104 to permit manipulation, treatment and/or decontamination of the casualty 124 by means of handling gloves 132 formed into the side of the treatment container 129.

The personnel 126 can observe their operations through a window 134 on the top of the treatment container 129. The treatment container 129 may contain treatment and/or decontamination apparatus 135 for treating the casualty 124. In lieu of separate treatment apparatus, handling apparatus 136 and treatment means 137 such as decontaminates, shown in phantom in FIG. 1, can be incorporated into the inner enclosure 104.

The access apparatus 128 thus protects attending personnel 126 during treatment of a contaminated casualty 124 by means of restricting the chemical contaminant to the interior of the inner enclosure 104 and the treatment container 129. The access apparatus 128 closely parallels the apparatus utilized for treating casualties in a contaminated area as disclosed in U.S. patent application Ser. No. 501,733, filed June 6, 1983, assigned to the same assignee as the present application and hereby incorporated by reference.

Figure 6:
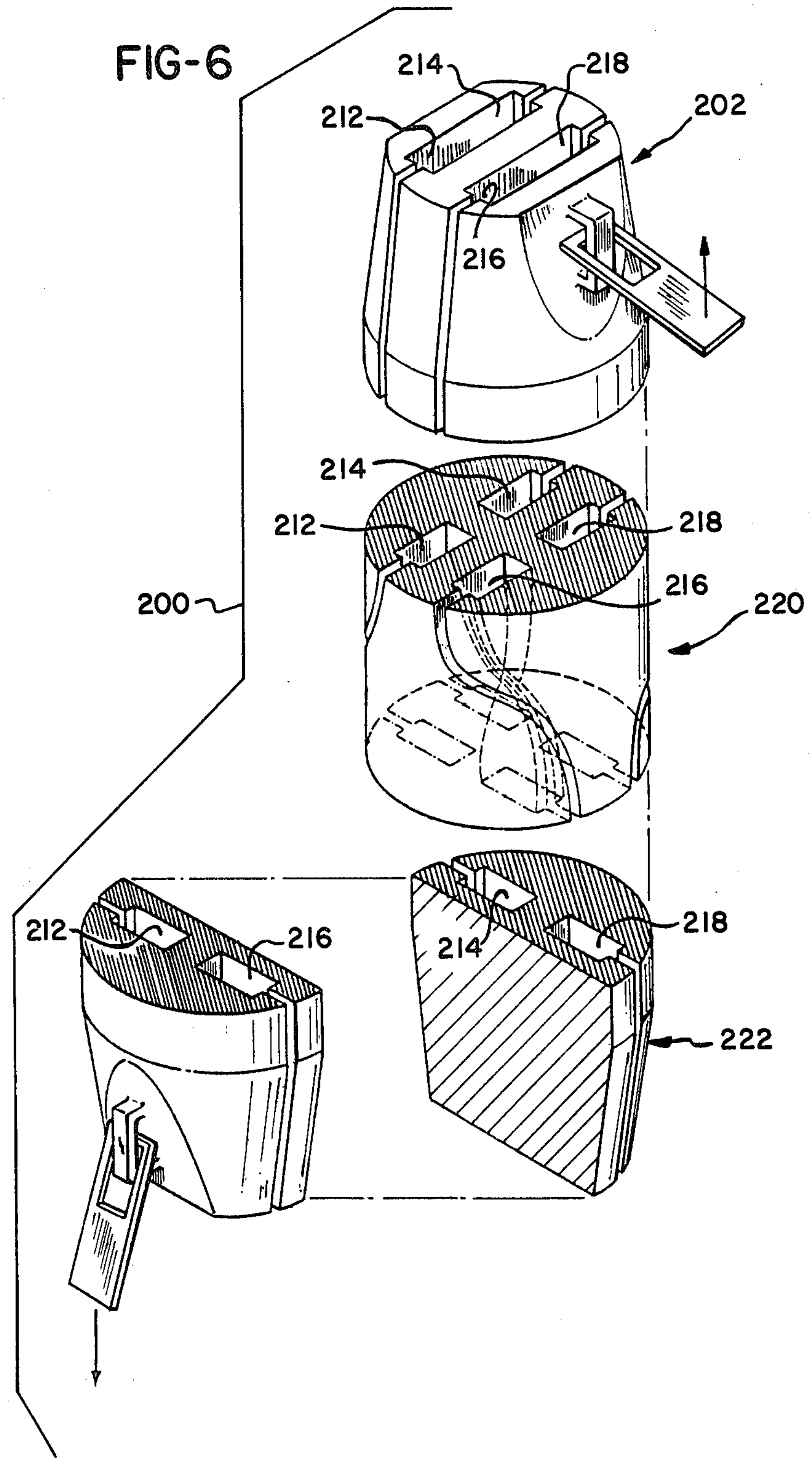
FIGS. 6 and 7 show an illustrative embodiment of an interlocking fastener device for use in the present invention.
Figure 7:
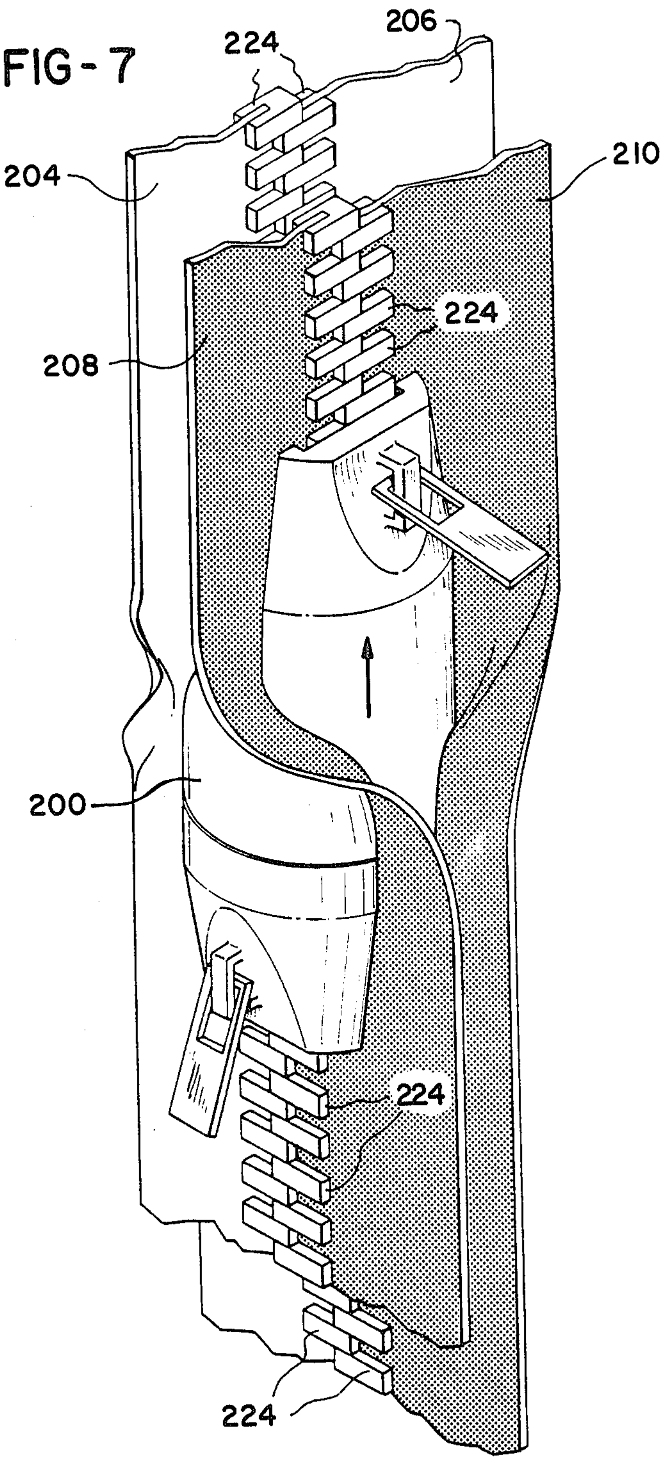

An illustrative embodiment of an interlocking fastener device suitable for utilization in the present invention is shown in FIGS. 6 and 7. For ease of understanding, a slide member 200 is shown as a multi-piece member in FIG. 6; however, it is to be understood that for specific applications of the device, various pieces may be separated or joined together to perform the fastening operation. To assist in the description of the fastener, the slide member 200 of the fastener system will be examined in three segments.

The first segment 202 receives two joined tape member pairs (such as tape members 204 and 206 or tape members 208 and 210 as shown in FIG. 7) through contiguous channels 212 and 214 and contiguous channels 216 and 218. The first segment 202 is of conventional design as described in U.S. Pat. No. 2,229,216 in which the contiguous channels 212–218 diverge at the exit end of the first segment.

The second segment 220 is critical to the operation of the fastener device for utilization in the present invention. Each of the four channels 212–218 are twisted approximately ninety degrees in a helical fashion about a vertical axis, thus realigning the tape members into new pairs for entry into the third segment 222.

The third segment 222 of the slide member 200 is basically identical in structure with the first segment 202. The orientation of the third segment, though, is different, having been rotated 180° about a horizontal axis and 90° about a vertical axis with respect to the first segment's position. Due to this orientation, the third segment will join the individual tape members into new pairs. The channels merge as 212 and 216, 214 and 218, in the third segment 222 guiding the tape members together. At the exit end of the third segment 222, channels 212 and 216 are now contiguous as are 214 and 218.

FIG. 7 is a perspective view of the integrated component described as three separate segments in FIG. 6 showing the pairs of fasteners which each comprise two tape members (204, 206 and 208, 210 respectively) and compatible interlocking parts 224 inserted into the slide member 200. The tape members are joined by the interlocking parts, here exemplified by zipper teeth although it is to be understood that the interlocking parts can be of many types.

These tape members are paired 204 with 206 and 208 with 210 before entry into the slide member 200. As the slide member 200 moves upward relative to the tape member pairs, as designated by the arrow, the tape pairs 204, 206 and 208, 210 are disconnected as a result of the diverging channels. Midway through the slide member, the tape members are no longer connected pairs but instead are four separate members in the process of being twisted or rotated, yet all the tape members are captured and protected from the external environment. The 90° twist of the separate members results in new pairs; the new arrangement pairs tapes 204 with 208 and tapes 206 with 210. Finally, as the channels merge to form contiguous pairs, the interlocking parts 224 of the tape members engage to join the tape pairs as just described.

Additional details of the illustrative fastener device shown in FIGS. 6 and 7, as well as alternate embodiments of that fastener, are disclosed in U.S. patent application Ser. No. 452,658 filed Dec. 23, 1982, entitled "Interchange Mechanism for Multiple Fasteners", assigned to the same assignee as the present application and hereby incorporated by reference.

In view of the teachings of the present application, various modifications and alternate embodiments will be apparent to those skilled in the art. For example, it will be recognized that a variety of fasteners can be utilized in the present invention. Such alternative fasteners could take the form of the fasteners described in U.S. patent application Ser. No. 390,100, previously referred to above.

Thus, while the method herein described and the form of apparatus for carrying the method into effect constitute a preferred embodiment of this invention, it is to be understood that the invention is not limited to this precise method and form of apparatus, and that changes may be made in either without departing from the scope of the invention which is defined in the appended claims.

What is claimed is:

1. Apparatus for the evacuation of a contaminated casualty to an uncontaminated enclosure having at least one flexible panel with an opening therethrough and first fastener means connected to said opening and operable for repeated opening and closing thereof, said evacuation apparatus comprising:

an outer enclosure having at least one flexible panel with a casualty entry opening therein;

an inner enclosure having at least one flexible panel with a casualty entry opening therein and being positioned within said outer enclosure such that said casualty entry openings in said flexible panels of said inner and outer enclosures are adjacent to one another;

second fastener means attached to said casualty entry openings and operable for opening and closing said casualty entry openings to permit access to the interior of said inner enclosure, said second fastener means further providing for closing the space between said inner and outer enclosures when said casualty entry openings are opened such that said space remains uncontaminated regardless of operation of said second fastener means;

a casualty extraction opening in said flexible panel of said outer enclosure; and third fastener means attached to said casualty extraction opening and operable for opening and closing said casualty extraction opening, said third fastener means being compatible with at least a portion of said first fastener means to permit coupling of said outer enclosure to said uncontaminated enclosure whereby the interior of said uncontaminated enclosure communicates with the uncontaminated interior of said outer enclosure such that a contaminated casualty encapsulated within said inner enclosure can be evacuated to said uncontaminated enclosure.

2. Evacuation apparatus as claimed in claim 1 wherein said inner and outer enclosures comprise bags and said flexible panels comprise sidewalls of said bags.

3. Evacuation apparatus as claimed in claim 1 wherein said second fastener means comprises:

mating parts of continuous flexible fastener strips connected to the sides of said casualty entry openings; and an elongated slide member having four generally elongated passages including merging parts of said passages at one end of said slide member adapted to receive said parts of said fastener strips, said passages separating in the central part of said slide member and having parts merging different ones of said passages at the other end of said slide member to bring said fastener strips into contiguous relation with the mating parts arranged such that one part of each fastener strip is mated with an opposite part of the other fastener strip by moving said slide member along said strips simultaneously and progressively separating the mating parts of the fastener strips and joining the parts with opposite parts of the other fastener strip, whereby joining and/or separating the edges of said casualty entry openings is accomplished to form and/or close a distendable passage through said panels of said enclosures, said passage being defined by the parts of the two joined fastener strips which close the space between said inner and outer enclosures when said casualty entry openings are opened.

4. Evacuation apparatus as claimed in claim 1 further comprising apparatus for safe access to a contaminated casualty encapsulated within said inner enclosure, said access apparatus comprising:

container means having at least one flexible panel with an opening therethrough;

fourth fastener means for closing said opening in said container means, said fourth fastener means being compatible with at least a portion of said second fastener means to permit coupling of said container means to said inner enclosure such that the interior of said container means communicates with the interior of said inner enclosure;

handling means in said container means for permitting sealed insertion of the hands of attending personnel into the interior of said container means and said inner enclosure; and observation window means in said container means whereby attending personnel obtain access to the contaminated casualty without being contaminated.

5. Evacuation apparatus as claimed in claim 1 further comprising:

treatment means for treating a contaminated casualty encapsulated within said inner enclosure; and handling means in said inner enclosure for permitting sealed manipulation therewithin for attending to said casualty.

6. A method for protecting attending personnel and facilitating the evacuation of a contaminated casualty to an uncontaminated treatment enclosure having at least one flexible panel with an opening therethrough and first fastener means connected to said opening and operable for repeated openings and closings thereof, said method comprising the steps of:

providing a casualty evacuation container having inner and outer enclosures;

opening said casualty evacuation container to expose the interior of said inner enclosure and close the space between said inner and outer enclosures to prevent contamination of said space;

placing a contaminated casualty into the interior of said inner enclosure;

closing said casualty evacuation container to encapsulate said contaminated casualty into said inner enclosure and separate said inner and outer enclosures, the space therebetween remaining uncontaminated;

connecting said outer enclosure to said first fastener means to form a closed passageway between said outer enclosure and said uncontaminated treatment enclosure; and moving said contaminated casualty encapsulated within said inner enclosure from said outer enclosure into said uncontaminated treatment enclosure.

7. A method as claimed in claim 6 further comprising the step of connecting container means including treatment supplies therewithin and handling means for manipulation of said treatment supplies to said inner enclosure whereby said contaminated casualty can be attended to while encapsulated within said inner enclosure.

* * * * *